United States Patent [19]

Meisner et al.

[11] Patent Number: 4,585,754
[45] Date of Patent: Apr. 29, 1986

[54] STABILIZATION OF PROTEINS AND PEPTIDES BY CHEMICAL BINDING WITH CHONDROITIN

[75] Inventors: Lorraine F. Meisner; Michael R. Schinitsky, both of Madison, Wis.

[73] Assignee: Valcor Scientific, Ltd., New York, N.Y.

[21] Appl. No.: 679,087

[22] Filed: Dec. 6, 1984

Related U.S. Application Data

[62] Division of Ser. No. 569,038, Jan. 9, 1984, abandoned.

[51] Int. Cl.$^4$ .................. C07K 9/00; C07K 17/10; C12N 11/02; C12N 9/96
[52] U.S. Cl. ........................ 514/8; 260/112 R; 260/112.7; 260/123.7; 435/178; 435/188
[58] Field of Search ............. 424/177; 260/112 R, 260/123.7; 435/188, 178; 514/8

[56] References Cited

U.S. PATENT DOCUMENTS

| | | | |
|---|---|---|---|
| 3,527,225 | 9/1970 | Smith | 260/112 R |
| 3,847,890 | 11/1974 | Green | 260/112 R X |
| 4,003,792 | 1/1977 | Mill et al. | 260/112 R X |
| 4,017,605 | 4/1977 | Huber et al. | 260/113 X |
| 4,022,888 | 5/1977 | Huber et al. | 260/113 X |
| 4,042,689 | 8/1977 | Huber et al. | 260/113 X |
| 4,059,572 | 11/1977 | Nakamura et al. | 260/112 R |
| 4,060,081 | 11/1977 | Yannas et al. | 128/156 |
| 4,105,760 | 8/1978 | Szejtli et al. | |
| 4,280,954 | 7/1981 | Yannas et al. | 260/123.7 |
| 4,346,174 | 8/1982 | Yasuda | 260/113 X |
| 4,350,629 | 9/1982 | Yannas et al. | 260/123.7 |
| 4,409,138 | 11/1983 | Maitz | 260/112 R |
| 4,489,065 | 12/1984 | Walton et al. | |

FOREIGN PATENT DOCUMENTS

| | | | |
|---|---|---|---|
| 0021626 | 2/1984 | Japan | 260/112 R |
| 97467 | 2/1961 | Norway | |

OTHER PUBLICATIONS

Boccu et al., *Pharmacological Research Communications*, 14, 113–120 (1982).
Baranov et al., *Bulletin of Experimental Biology in Medicine*, 95, 357–359 (1983).
Carbohydrate Research, vol. 16, No. 1.1, 1971, pp. 199–205, Danishevsky et al.
Biochimica et Biophysica Acta, 703, 21–25, 1982, Snowden.
Chem. Abstracts, vol. 98, 1983, 166902u, Walton et al., effective date Jan. 20, 1983.
Abuchowski et al., *Enzymes as Drugs*, ed. by Holcenberg and Roberts, New York: John Wiley & Sons (1981), pp. 367–383.

*Primary Examiner*—Howard E. Schain
*Attorney, Agent, or Firm*—Barnes & Thornburg

[57] ABSTRACT

Peptides, polypeptides, proteins, proteinaceous hormones, and enzymes are modified by covalently bonding chondroitin thereto, whereby their stability toward in vivo degradation is increased.

10 Claims, 1 Drawing Figure

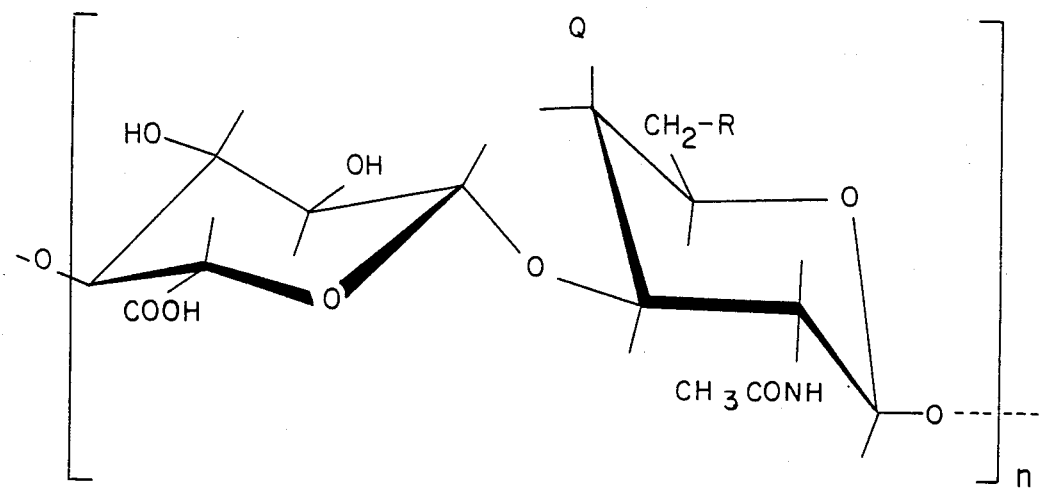
CHONDROITIN REPEATING UNIT

STABILIZATION OF PROTEINS AND PEPTIDES BY CHEMICAL BINDING WITH CHONDROITIN

This is a division of application Ser. No. 569,038, filed Jan. 9, 1984 and now abandoned.

This invention relates to substances of the class of peptides, polypeptides, and proteins, and to the stabilization thereof in vivo.

Proteins and enzymes, as well as other peptides and polypeptides, tend to be rapidly degraded in the animal and human body and generally in aqueous solutions containing acids, bases, amidases, and/or esterases. For this reason, such substances are of limited industrial, diagnostic, and therapeutic use. It has heretofore been reported that stabilization of these substances can be achieved in some degree by chemically binding them to a polymer, but such binding tends to adversely modify or even destroy the desired property of the substance in question and/or may produce unforeseen toxic effects, making the modified substance bioincompatible. Additionally, the added polymer may not be biodegradable within the animal or human body and thus may build up to toxic levels even though the bound substance is released and produces the intended effect.

The present invention provides a novel class of modified peptides, resistant to metabolism and degradation in the animal or human body, which are prepared by chemically linking the peptide to a chondroitin. The advantages of using the chondroitins lie in the fact that such molecules are found throughout the body, are biocompatible, are not species-dependent, and yield combination products with peptides which, when introduced into the body, act directly to produce the effects of the original, unmodified peptides in a prolonged manner, but without intervening hydrolysis, saponification, de-amidation, or other form of so-called "sustained-release" disproportionation.

It is thus an object of the present invention to convert peptides and peptide-like substances into a modified form, stable in vivo.

Another object is to convert such substances into a form having a sustained effect in the body.

Other objects of the invention and its advantages over the prior art will be apparent from the present description.

A discussion of the stabilization of certain proteinaceous substances is given by Abraham Abuchowski and Frank Davis in a chapter entitled "Soluble Polymer-Enzyme Adducts" in the book *Enzymes As Drugs*, Ed. by Holcenberg and Robers, New York: John Wiley & Sons (1981). Abuchowski coupled various enzymes with polymeric materials to produce soluble adducts with biological properties suitable for in vivo use. As polymeric materials, Abuchowski used polyvinylpyrrolidone, dextran, polyethylene glycol, glycopeptide, desialized fetuin, desialized orosomucoid, lactose, polymaleic acid, poly-DL-alanine, and albumin.

Danishefsky and Siskovic, *Carbohydrate Research*, 16, 199 (1971), while studying the structure-function implication of the glycosaminoglycans, found that the amino function of certain amino acids can be covalently linked to the carboxyl group of a glycosaminoglycan. Danishefsky reacted peptides, including enzymes and insulin, with polysaccharides, including mucopolysaccharides and specifically chondroitin, to produce derivatives for immuno-chemical investigation. With chondroitin, Danishefsky reacted only glycine methyl ester (not a peptide), and the reference is silent as to any stabilization of a peptide for in vivo administration.

Mill et al U.S. Pat. No. 4,003,792 teaches that proteins may be bound to acid polysaccharides of plant origin, specifically alginic acid, pectic acid, celluronic acid, and carageenan. Such polysaccharides are food carbohydrates, alien to the blood and tissues of animals, and are clearly distinct both chemically and physiologically from the chondroitins used in the present invention.

Yannas and Burke U.S. Pat. Nos. 4,060,081 and 4,059,572 use the ionic properties of mucopolysaccharides (an older term essentially coextensive with the glycosaminoglycans) to flocculate or complex ionically with proteins. For example, an artificial skin formulation was prepared from chondroitin sulfate and collagen.

Walton et al, *Chemical Abstracts*, 98, 380, abstract 166902U (1983), disclose that chondroitin sulfate can be combined with drugs to create prodrugs which, following enzymatic or other degradation of the chrondroitin, release the active drug. Unlike the Walton et al product, the product of the present invention is not a prodrug; to the contrary, our chondroitin-peptide combination is itself the drug, and produces the same effect as the original peptide except that the peptide is, in effect, stabilized and its activity is significantly prolonged. The effect is achieved even if a portion of the chondroitin is degraded in vivo, leaving chondroitin of lower molecular weight linked to the peptide.

Snowden, *Biochemica et Biophysica Acta*, 703, 21-25 (1982), observed that collagen fibrils were stabilized in a solution of chondroitin sulfate, and that the stability increased with greater concentrations of chondroitin. No chemical linkage was involved, however, but only physical proximity of collagen and chondroitin in solution. Moreover, it is not therapeutically feasible to inject enough chondroitin sulfate to produce such an effect in the body, even if the stabilization of collagen fibrils were a meaningful operation in that context.

Boccu et al, *Pharmacological Research Communications*, 14, 113-120 (1982), indicated that the use of a synthetic polymer, polyethylene glycol, linked to a protein such as superoxide dismutase ("SOD") could increase its stability and protect it from denaturation and enzymatic digestion, thereby increasing its activity and its time in the circulation. Polyethylene glycol, however, being a synthetic polymer, is not natural to the animal or human body, and suffers from the usual drawbacks of such materials, noted above.

Baranov et al, *Bulletin of Experimental Biology and Medicine*, 95, 357-359 (1983), combined insulin with "polythenate," a synthetic polymer, and administered the product orally to rabbits with promising results. "Polythenate" is, of course, unrelated to the natural polymer chondroitin.

In accordance with the present invention, a chondroitin is reacted in a known manner with a pharmaceutically active substance of the broad class of the peptides as hereafter more fully defined to produce an ester and/or amide derivative thereof which is stable in vivo and exerts the pharmaceutical activity of the original peptide in a prolonged manner.

The repeating structural unit of the chondroitins is shown in the drawing. In the basic chondroitin structure, both Q and R are hydroxyl. The chondroitins occur most commonly in one of two forms, chondroitin-4-sulfate ("C4S"), in which the hydroxyl at Q is sulfated, and chondroitin-6-sulfate ("C6S"), in which the hydroxy at R is sulfated. It should be noted that for the present invention either form of chondroitin can be used, that the chondroitin and peptide are joined covalently, primarily by amide or ester linkages, and that chondroitin can be used over a wide range of molecular weights (e.g. from around 5,000 to 100,000 daltons). The enhanced stability is believed to be principally due to the cross-linkages which form after the covalent union of chondroitin and peptide. As will be seen from the drawing, a variety of functional groups are available in the chondroitins for covalent bonding (particularly carboxyl, COOH, and hydroxyl, OH) by way of ester links, —COOY, or amide links, —CONHY, with the hydroxy, OH, carboxyl, COOH, and amine, $NH_2$, groups of the peptides.

The present invention is applicable generally to the stabilization of peptides and polypeptides, including, without limitation, simple peptides, polypeptides, proteins, proteinaceous hormones, enzymes, and the like. All such substances are peptides in essence, in that they are strands of amino acids joined together via amide linkages. For convenience, the term "peptide" is used generically herein to refer to all such substances. Illustrative examples include superoxide dismutase, insulin, interferon, growth hormone, and peroxidase, all of which are typical labile proteins. Interferon is an especially apt example of a substance adapted for modification in accordance with the invention; because it is quickly degraded within the body when administered in the free form, it must be injected in high (often toxic) doses in order to exert its effect before being inactivated. When covalently bound to chondroitin, however, interferon can be used effectively at lower and fewer doses. Other illustrative peptides include asparaginase, glutamase, arginase, arginine deaminase, somatomedin, ACTH, FSH, LH, somatostatin, vasopressin, RNase, endorphins, enkephalins, and the enzymes associated with the more than 150 inborn errors of metabolism, such as hexosaminidase A, hexosaminidase B, alpha-glucosidase, beta-glucosidase, sphingomyelinase, and arylsulfatase.

The reaction of the chondroitin with the peptide starting material to obtain the novel substances of the present invention is carried out in a known manner, depending upon the functional groups involved.

Where the chondroitin and the peptide contain a hydroxyl group and a carboxyl group, respectively, the two can be reacted by use of a carbodiimide; or the carboxyl group can be converted to an acid chloride and reacted with the hydroxyl group; or the carboxyl group can be converted to a mixed anhydride and reacted with the hydroxyl group. All of these procedures and the conditions required therein are old and well known in the art. The same procedures can be used when the chondroitin and the peptide contain a carboxyl group and a hydroxyl group, respectively. In all such cases, the product is an ester.

When the chondroitin and the peptide substance contain a hydroxyl and an amino group, respectively (or vice versa), the reaction can be caused to proceed through formation of a carbamate bond via the activation of the hydroxyl to a chloroformate moiety with subsequent linking to the amine function. The procedure and proper reaction conditions are well known and conventional in the art. Similarly, a carbonate bond can be formed between two hydroxyl groups (on the chondroitin and on the peptide).

When the chondroitin and the peptide substance contain a carboxyl group and an amino group, respectively (or vice versa), the reaction is one of conventional amide formation under known conditions employing known procedures, eliminating a molecule of water between the two molecules. Where one or both of the starting materials contains more than one functional group, it may be desirable to protect groups that are not desired to react, in order to avoid obtaining a mixed product. These are techniques which are well known in the art.

The activity and stability of the chondroitin-peptide product can be varied in a number of ways; e.g. by changing the molecular ratio of chondroitin to peptide, by changing the molecular size of the chondroitin (usually employed in a molecular weight range of around 5,000 to 100,000 daltons), and by changing the degree of cross-linking between the chondroitin and the peptide, as well as the degree of cross-linking in the chondroitin itself.

Since chondroitin is a substance naturally found in every mammalian body, as well as every other cartilage-containing creature (from birds to sharks), chemically linking it to a peptide, protein, hormone, or enzyme cannot produce any unexpected toxic effects. Because chondroitin is completely biocompatible, and because it is also completely biodegradable in the body (unlike many synthetic polymers, and some natural ones like dextran), no problem can arise via build-up within the body.

The reaction products of the present invention are conveniently prepared for administration by dissolving in water or in an isotonic salt solution, or in cases where the product is less soluble, by comminuting and suspending in water or an isotonic salt solution. In the latter case, the product can also be dissolved in an appropriate organic solvent such as dimethylsulfoxide, dimethylformamide, or the like, diluted with water to form a colloidal suspension, and vacuum stripped or dialyzed against water to remove the organic solvent. The solution or suspension may appropriately contain from about 5 to about 500 mg. of product per milliliter as a suitable concentration for injection into the patient, and the volume injected is chosen to provide the desired drug dosage, which will, of course, vary with the drug substance.

The following specific examples, describing the application of the invention to superoxide dismutase ("SOD") and to insulin, will more fully illustrate the invention and the best mode now contemplated for carrying it out. SOD is a large protein molecule, with a molecular weight around 22,000 daltons, while the insulin molecule is relatively small, with a molecular weight around 6,000 daltons. Both of these proteins are very unstable in the body, SOD having a half-life of about five minutes, and insulin (which is subject to destruction by insulinase), about 15 minutes. In their native forms, neither can be effective by oral administration. SOD and insulin are considered to be representative of proteins in general, and were selected to illustrate the present invention because of their differences in molecular weights, structures and functions, one being a hormone (insulin) and the other an enzyme (SOD). Despite their many differences, both of these substances effectively illustrate the stabilization of proteins by chemical combination with chondroitin.

EXAMPLE 1

Superoxide Dismutase

To a solution of 5 mg. of superoxide dismutase ("SOD") in 1 ml. of water was added a solution of 5 mg. of chondroitin sulfate A (Sigma Chemical), a mixture of the 4- and 6-sulfates, in 1 ml. of water, and the mixture was adjusted to pH 4.75. A solution of 5 mg. of 1-ethyl-3-(3-dimethylaminopropyl)-carbodiimide hydrochloride ("EDC") in 0.5 ml. of water was added, and the mixture was stirred for six hours at room temperature, then dialyzed overnight against water. The mixture was further purified by chromatography using pH 7 phosphate buffer for elution. The purified product contained 72 percent of SOD linked to chondroitin.

The SOD-chondroitin sulfate A product was tested for stability against proteolytic digestion. An aqueous solution containing 10 mg./ml. of the product was incubated with 50 mcg./ml. of trypsin at pH 7.8 and 23 C, and aliquots were withdrawn from time to time and the SOD activity determined. For comparison, SOD alone with incubated with trypsin under the same conditions. After just over forty minutes, approximately 88 percent of the SOD-chondroitin product remained in the solution, compared with only about 8 percent of the unprotected SOD. This is a difference in stability of over eight-fold.

Inasmuch as trypsin is known to be a very specific protease, cleaving only at the arginine and lysine residues, a further test was carried out according to substantially the same procedure using pepsin, a much more vigorous protease. The pH was kept low (3.5), since the optimum pH for pepsin is known to about 1.0–1.5. Even at the lowest concentration of pepsin tested (500 ng./ml.), digestion was very fast, but there was some degree of protection by the chondroitin compared with unprotected SOD. At two minutes, the latter had been essentially all destroyed, while at three minutes approximately 5 percent of the former remained active.

Tests were also carried out in mice to compare the in vivo stability of the chondroitin-protected SOD with unprotected SOD. The mice received a 0.1 ml. intraperitoneal injection of one of the two preparations (10 mg./ml.). One hour later, blood specimens were taken and the sera were chromatographed (G-100) in phosphate buffer (50 mM, pH 7). Tests on the serum prior to elution showed only low levels of SOD in the control group, thus ruling out hemolysis during serum preparation. The test results showed that only 0.5 to 2 percent of the SOD-chondroitin preparation had been hydrolyzed at the end of one hour in vivo, at which time the serum contained nearly four times as much SOD as the controls. Nearly all of the SOD activity was found in the high-molecular-weight fraction of the eluate (greater than 100,000 daltons). The experiment demonstrates that the SOD-chondroitin preparation can be administered intraperitoneally, enter the circulatory system, and survive for many hours under the conditions tending to produce proteolytic degradation in vivo.

EXAMPLE 2

Insulin

A solution of chondroitin sulfate A sodium salt (50 mg. in 0.5 ml. of water) was mixed with an insulin solution (50 mg. in 2.5 ml. of water) and the mixed solution was adjusted to pH 1.6 with 1N hydrochloric acid. A solution of 50 mg. of 1-ethyl-3-(3-dimethylaminopropyl)carbodiimide hydrochloride ("EDC") in 0.5 ml. of water was added, the pH was adjusted to 4.6, and the mixture was stirred for six hours at room temperature, after which it was adjusted to pH 7.0, dialyzed overnight against water, and lyophilized. The yield of the chondroitin-insulin reaction product was 50 percent of theory.

Comparative tests were carried out on the chondroitin-insulin reaction product and on unprotected (free) insulin to measure their relative susceptibility to proteolytic degradation. For this purpose, protease K was chosen because it is a general, non-specific proteolytic enzyme, cleaving at many sites. Thus, it affords a better idea of the sensitivity of the protected insulin to proteolysis than would be given by the more specific proteases such as trypsin or chymotrypsin, which act upon the insulin molecule at only a few specific cleavage sites. The precise conditions of the tests were as follows:

For the "free" insulin, one milligram of insulin was suspended in 1.0 ml. of phosphate buffer, pH 7.5, to which was added 10 microliters of a protease K solution containing 1 mg. of the enzyme per milliliter of water; and after a desired exposure time the entire solution was chromatographed on a Sephadex G-50 column, the elution of protein and peptides being monitored by observing the absorbance at 278 nm. A separate test was carried out for each desired exposure time. The net loss of peptide in each test was determined by pooling all fractions outside the void volume, drying them under vacuum, suspending them in 1.0 ml. of buffer, and analyzing for peptides by the Biuret method.

For tests on the chondroitin-insulin reaction product, 2 mg. of the latter were used, equivalent to 1 mg. of free insulin.

The results of the above tests demonstrate that the chondroitin-insulin reaction product is about 7 times as stable as free insulin, measured by their half-lives during proteolysis, which is 15 minutes for the free insulin compared to 105 minutes for the protected insulin.

The above results tend to be confirmed by further tests on the non-enzymatic degradation of chondroitin-protected insulin during incubation in water at 37° C. At the end of twelve days, only about 22 percent of the insulin had been released in free form. The chondroitin preparation, being highly cross-linked, could be partially recovered by centrifugation at 50,000 g for 0.5 hr, and showed no signs of turbidity (i.e., denaturation).

Animal studies were carried out to compare the efficacy of the bound and free insulin in lowering blood glucose levels. Female CD-1 Swiss white mice averaging 20 g in weight were fasted overnight and used in groups of four. The insulins were injected subcutaneously, and blood specimens (50 microliters, by retroorbital bleeding) were taken at intervals of 0.5, 3, 6, and 24 hours. The free insulin was given in doses of 1.4, 2.8, 5.7, 11.4, 22.8, and 45.5 micrograms; the chondroitin-insulin preparation at doses of 46, 91, 121, 151 and 182 micrograms. The mice receiving free insulin at doses of 5.7 micrograms and above were comatose in one-half hour, and at all levels there was a significant rebound glucose level by 24 hours. In contrast, none of the mice receiving the chondroitin-insulin preparation became comatose, and their blood glucose levels showed continuing depression even after 24 hours, thus demonstrating the prolonged in vivo activity of the preparation.

Similar tests were carried out in mice to compare the chondroitin-insulin preparation in duration of action with Ultralente, an insulin preparation having sustained action owing to its being complexed with zinc, which keeps it in depot form longer than free insulin. Tests on the two preparations were carried out at the same doses (5.7, 11.4, 22.8, and 44.5 micrograms) and for the same time periods. With Ultralente, all of the animals were either very lethargic or comatose after 45 minutes. No such effects were produced by the chondroitin-insulin preparation. Also, Ultralente did not achieve nearly as good glucose depression as the chondroitin-insulin preparation, and a pronounced rebound effect was observed at all but the two highest doses.

The above tests demonstrate that the chondroitin insulin preparation has a substantially higher level of safety than free insulin or Ultralente insulin. Moreover, the resistance of the preparation to proteolytic degradation makes it a prime candidate for oral administration, preferably in a dosage form protected from the stomach environment by an enteric coating.

While we have described our invention with reference to certain specific embodiments thereof, including starting materials, process steps, materials, and conditions, and product forms and formulations, it is to be understood that such matters are illustrative only and are not intended by way of limitation. Numerous modifications and equivalents will be readily apparent to those skilled in the art from the above description and the appended claims.

What is claimed is:

1. In a method of administering biologically active peptides to enhance or achieve a desired physiological response known to be elicited by said peptide, the improvement which comprises administering said peptide in combination with chondroitin chemically bonded thereto to prolong the desired response.

2. The method of claim 1 wherein said peptide is a protein.

3. The method of claim 1 wherein said peptide is a proteinaceous hormone.

4. The method of claim 3 wherein said proteinaceous hormone is insulin.

5. The method of claim 1 wherein said peptide is an enzyme.

6. The method of claim 5 wherein said enzyme is superoxide dimutase.

7. The method of claim 1 wherein said chondroitin is chondroitin-4-sulfate.

8. The method of claim 1 wherein said chondroitin is chondroitin-6-sulfate.

9. The method of claim 1 wherein said chondroitin has a molecular weight between about 5,000 and about 100,000 daltons.

10. A method for prolonging the desired physiological response known to be elicited upon administration of a biologically active peptide, which method comprising administering said peptide in a biologically active stabilized form consisting essentially of said peptide having chondroitin covalently bonded thereto.

* * * * *